United States Patent [19]

Hibino et al.

[11] 4,151,658

[45] May 1, 1979

[54] BED CLOTHES DRYING DEVICE

[75] Inventors: Shigetoshi Hibino; Atsushi Oguri, both of Nakatsugawa, Japan

[73] Assignee: Mitsubishi Denki Kabushiki Kaisha, Tokyo, Japan

[21] Appl. No.: 859,711

[22] Filed: Dec. 12, 1977

[30] Foreign Application Priority Data

Dec. 13, 1976 [JP] Japan ........................... 51-166840[U]
Feb. 23, 1977 [JP] Japan ........................... 52-220877[U]

[51] Int. Cl.$^2$ .......................... F26B 19/00; A61F 7/06

[52] U.S. Cl. .................................... 34/243 R; 126/205

[58] Field of Search ........................ 34/243 R; 126/205

[56] References Cited

U.S. PATENT DOCUMENTS

| | | | |
|---|---|---|---|
| 2,122,964 | 7/1938 | Sweetland | 34/243 R X |
| 2,590,026 | 3/1952 | Marx | 126/205 UX |
| 2,695,413 | 11/1954 | Maat | 126/205 UX |
| 3,711,958 | 1/1973 | Lepage | 34/243 R X |

*Primary Examiner*—Leonard H. Gerin
*Attorney, Agent, or Firm*—Oblon, Fisher, Spivak, McClelland & Maier

[57] ABSTRACT

A bed clothes drying device comprises a hot air supplier having a blower and a heater which is connected to an air inlet and a hot air outlet and a bag which is connected through a joint pipe to the hot air outlet and filled out under a blow pressure given by feeding a hot air from the hot air supplier to discharge the hot air through the sheet of the bag and which has flexibility and air-permeability with a resistance of 1.75 to 3.75 $mmH_2O$ to air flow of 0.7 to 1 $m^3/min$. The bag is disposed between a bed and a coverlet to dry the bed and the coverlet with the hot air and the bag has an improved structure.

6 Claims, 10 Drawing Figures

BED CLOTHES DRYING DEVICE

BACKGROUND OF THE INVENTION

1. Field of the Invention

The present invention relates to a bed clothes drying device, which drys a bed and a coverlet to feed a hot air through a sheet of a bag which is connected to a hot air supplier.

2. Description of the Prior Art

In usual, a bed and a coverlet are moistured with moisture perspired from a body during sleeping. Accordingly, they have been dried under exposing to sunlight with suitable intervals. When rainy or cloudy days continue, the bed and the coverlet can not be dried under sun-light whereby comfortable sleep can not be enjoyed.

SUMMARY OF THE INVENTION

It is an object of the present invention to provide a bed clothes drying device which easily drys a bed and a coverlet (including bed cover) regardless weather condition.

The foregoing and other objects of the present invention have been attained by providing a bed clothes drying device which comprises a hot air supplier having a blower and a heater which is connected to an air inlet and a hot air outlet and a bag which is connected through a joint pipe to the hot air outlet and filled out under a blower pressure given by feeding a hot air from the hot air supplier to discharge the hot air through the sheet of the bag and which has flexibility and air-permeability with a resistance of 1.75 to 3.75 $mmH_2O$ to air flow of 0.7 to 1 $m^3$/min. The bag can be a flat rectangular shape and it is used by disposing it between the bed and the coverlet which are dried by the hot air permeated through the sheets of the bag.

In the other embodiments, the bag can have certain improved structures. The peripheral part of the bag can be formed with an air-impermeable material whereby when the bag is disposed between the bed and the coverlet, the leakage of hot air directly discharged through the gaps between the bed and the coverlet.

The permeabilities of the upper and lower sheets can be different whereby when the bag is disposed between the bed and the coverlet, the sheet of the bag having higher air-permeability is faced to the bed side having much moisture.

The permeability of one sheet can be partially different so as to face the part of the sheet having higher air-permeability to the part of the bed contacting with a shoulder and a hip of a body which perspire in high degree.

The air-permeability can be increased by forming many fine holes being larger than cloth stitch of the bag so as to prevent excess fill-out.

A plurality parts between both side sheets can be connected with detouchable joint elements so as to prevent the break of the bag by detouching the joint elements when a pressure at a part of the bag is temporarily raised by trampling down.

A plurality of openings are formed on the bag and one opening is connected to the joint pipe for connecting to the hot air supplier and the other opening is closed with a plug whereby when the pressure at a part of the bag is raised, the plug is to prevent the break of the bag by detouching it so as to discharge the hot air through the opening.

BRIEF DESCRIPTION OF THE DRAWINGS

Various objects, features and attendant advantages of the present invention will be more fully appreciated as the same becomes better understood from the following detailed description of the present invention when considered in connection with accompanying drawings, wherein like reference numerals designate identical or corresponding parts throughout the several views in which.

DETAILED DESCRIPTION OF THE PREFERRED EMBODIMENTS

Figure 1:
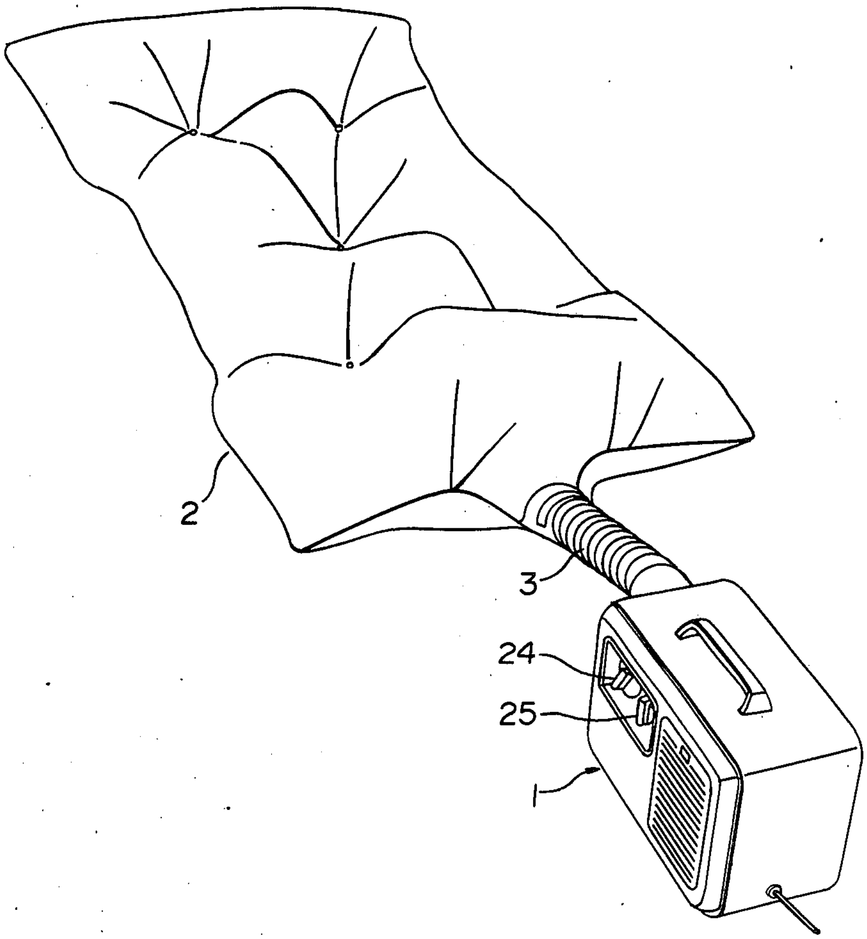
FIG. 1 is a schematic view of one embodiment of the bed clothes drying device.

Referring to the drawings, certain embodiments of the bed clothes drying device of the present invention will be illustrated.

In the specification, a bed includes a blanket under a body and a coverlet includes a blanket over a body and a bed cover.

FIG. 1 shows an appearance of the drying device of the present invention wherein the reference numeral (1) designates a hot air supplier and (2) designates a bag connected through a joint pipe (3) to the hot air supplier (1).

Figure 2:
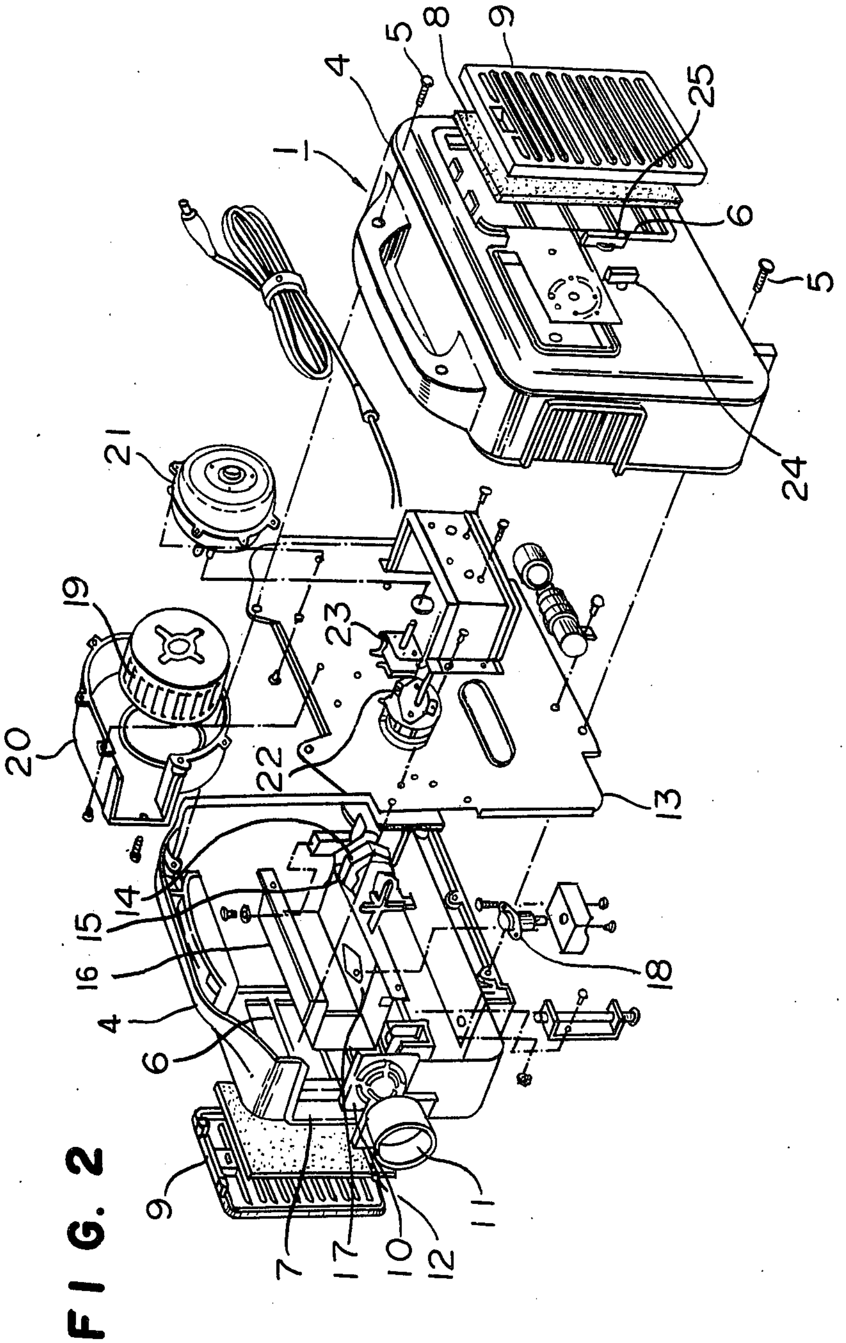
FIG. 2 is a schematic view of disassemble parts of a hot air supplier.

FIG. 2 shows a detailed structure of the hot air supplier (1) wherein the reference numeral (4) designates a casing made of ABS resin which can be separated into two parts and two parts are usually mounted to one body with screws (5).

Air inlets (6) are formed on both side surfaces of the casing (4) and a hot air outlet (7) is formed at the upper part of the casing (4) and a filter (8) and a grid (9) are filled on the air inlet (6); and a frame (10) and a connection flange (11) are disposed to hold the peripheral part of the hot outlet (7) and are mounted in one piece with screws. A metal mounting plate (13) is held between the right and left segments of the casing (4) and an electric heater (14) is disposed inside of the hot air outlet (7) and the electric heater (14) is wound on a glass rod (15). A window cylinder (16) is made of a metal plate to cover and to hold the glass rod (15) and the window cylinder (16) is mounted on the metal mounting plate (13). An insulating plate (17) is bonded to the inner surface of the window cylinder (16) and a thermostat (18) is fitted. A fan (19) is faced to the window cylinder (16) and a guide casing (20) for the fan, a fan motor (21), a timer motor (22) and a switch (23) are mounted on the metal mounting plate (13). Dials (24), (25) for the switch and the timer are fitted.

Figure 3:
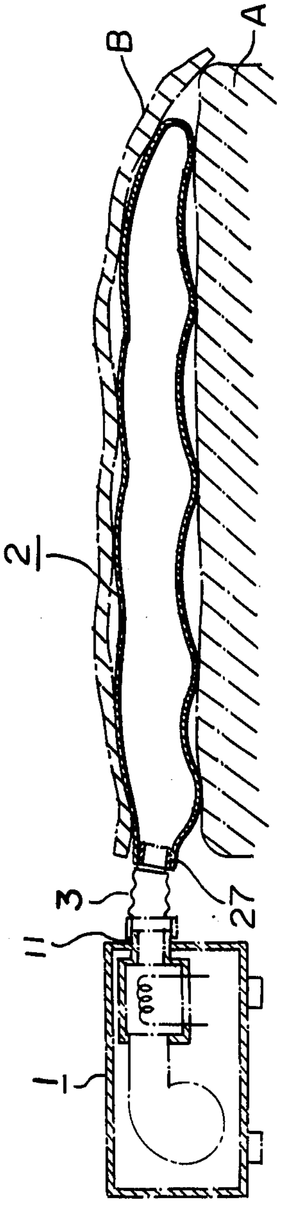
FIG. 3 is a sectional view of a bag of the drying device.
Figure 4:
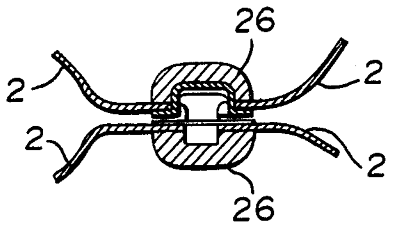
FIG. 4 is a sectional view of joint elements for jointing the upper and lower sheets of a bag.
Figure 5:
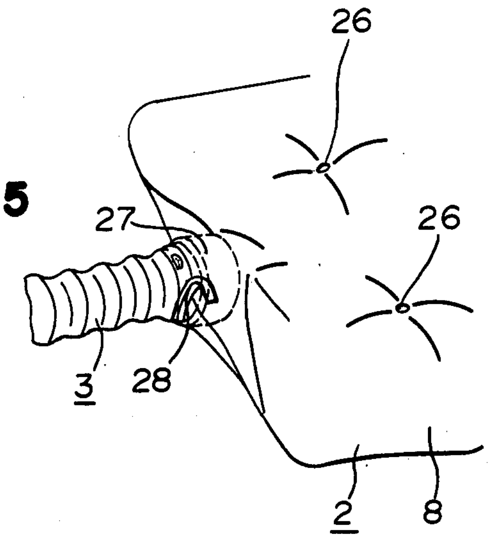
FIG. 5 is a schematic view of a joint pipe connecting to the bag.

FIGS. 3 to 5 show structures of the bag (2). The bag is formed by sewing together sheets of nylon taffeta (263 filaments per $inch^2$) which have flexibility and air-permeability (to give a pressure of 1.75 to 3.75 $mmH_2O$ under feeding air at a rate of 0.7 to 1 $m^3$/min.)

in a form of a flat rectangular shape having a length of 175 inch and a width of 88 inch.

The upper and lower sheets of the bag (2) are jointed with joint elements (26) such as hooks at plural parts as shown in FIG. 4.

As shown in FIG. 5, one end of the joint pipe (3) is inserted into a joint opening (27) of the bag to connect them and they are fastened with a band (28). The other end of the joint pipe (3) is fitted to the connecting flange (11) by inserting the joint pipe into the flang. The joint pipe (3) is a cylindrical sheet made of rubber coated nylon cloth having spiral wire core.

Figure 6:
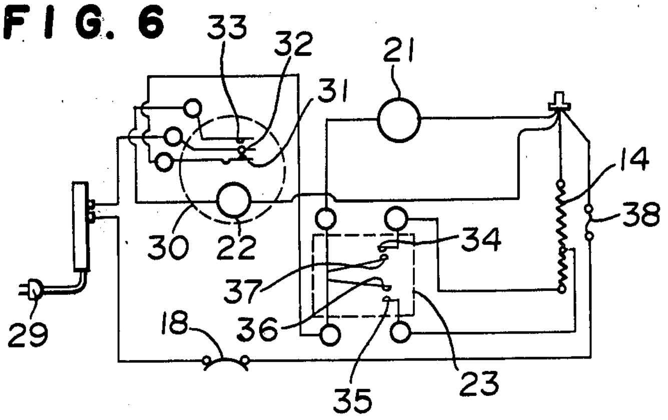
FIG. 6 is a circuit diagram used in the drying dive.

FIG. 6 is a circuit diagram wherein the reference numeral (29) designates a power source plug socket; (30) designates a timer; (22) designates a timer motor; (31), (32) and (33) designate contacts of the timer; (23) designates a switch; (34), (35), (36) and (37) designate contacts of the switch; (21) designates a fan motor; (18) designates a thermostat which is set to 59° C.; (38) designates a fuse which is melted at 226° C. and (14) designates an electric heater (600 W).

The operation of the embodiment of the invention will be illustrated.

When three contacts (31), (32), (33) of the timer (30) is cut off by the operating dial (24), the current fed to the fan motor (21) and the electric heater (14) is cut off. When the contacts (31), (32) of the timer (30) is contacted by the dial (24) from said stop condition, the conductive condition set by the switch (23) is given to feed the current only to the fan motor (21). When the contacts (35), (36) are connected, the current is fed to the fan motor (21) and a part of the electric heater (14). When all of the contacts (34), (35), (36), (37) are connected, the current is fed to the fan motor (21) and all of the electric heater (14).

When all of the contacts (31), (32), (33) of the timer (30) are connected by the dial (24), the current is also fed to the timer motor (22) to stop it after maintaining the conductive condition resulted by the switch (23) for the specific time.

In the condition feeding the current to the fan motor (21) and the heater (14), air is sucked through the air inlet (6) into the casing (4) by the fan (19) and air is heated to be hot air by passing around the heater (14) and the hot air is fed through the joint pipe (3) into the bag (2), and it is discharged through the sheet of the bag (2).

The bag (2) is disposed between the bed (A) and the coverlet (B) so as to be held. The hot air discharged through the sheet of the bag (2) is passed through the bed and the coverlet whereby the moisture of them is discharged together with the hot air. As the result, when the bag (2) is disposed between the bed (A) and the coverlet (B), the bed and the coverlet can be easily dried in the condition for sleeping.

Figure 7A:
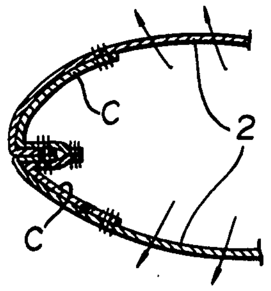
FIGS. 7 to 9 respectively show the sectional views of the other embodiments of the bag.
Figure 7B:
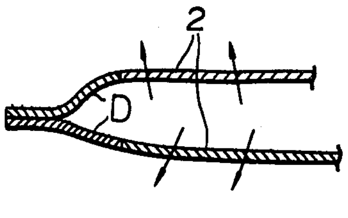

In said embodiment, all of the sheets of the bag (2) is formed by a cloth having uniform air-permeability. Thus, it is possible to cover the peripheral part with an air-impermeable cloth (C) as shown in FIG. 7(*a*) or to form the peripheral part (D) having an air-impermeable material as shown in FIG. 7(*b*), whereby the leakage of the hot air discharged through the gap between the bed and the coverlet can be minimized when the bag is held between the bed and the coverlet.

The material and the sheet structure can be selected to give different air-permeability to the upper and lower sheets of the bag. Thus, the sheet having high air-permeability can be disposed to the side of the bed containing much moisture to satisfactorily dry the bed.

Figure 8:
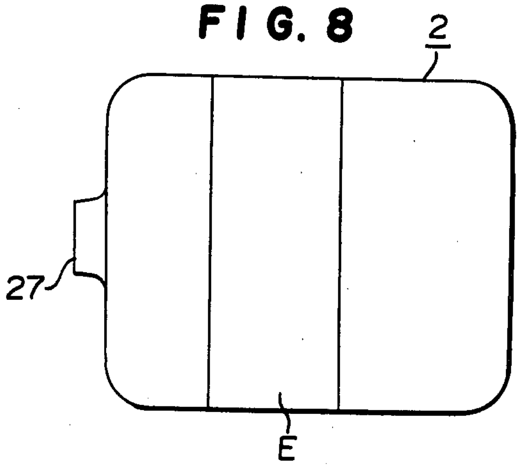

It is also possible to give high air-permeability at the parts E of one sheet of the bag contacting with a shoulder and a hip as shown in FIG. 8, whereby the bed at the parts contacting with the shoulder and the hip of the body which perspire in high degree can be satisfactorily dried.

Figure 9:
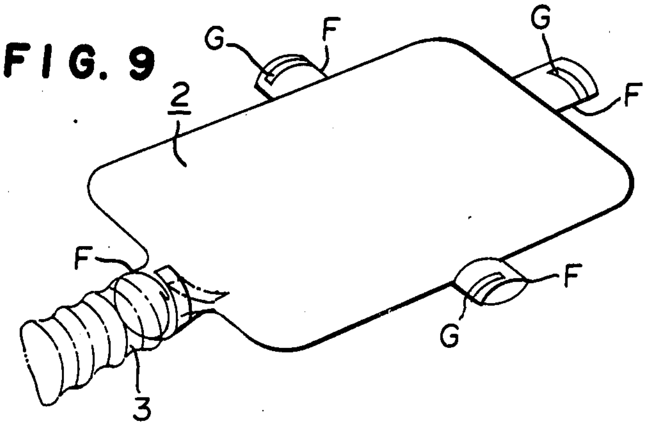

As shown in FIG. 9, a plurality of joint openings (F) can be formed on the bag. The joint pipe (3) is connected to one opening (F) and the other opening (F) are closed with a plug (G) whereby when a person step on the bag to partially increase the pressure in the bag (2), the plug (G) fitted to the joint opening (F) is taken out to discharge the hot air and the break of the bag can be prevented.

In the embodiments of FIGS. 3 to 5, the joint elements (26) such as hooks are disconnected to fill out the other part when one part is pressed by the step on.

What is claimed is:

1. A bed clothes drying device which comprises a hot air supplier having a blower and an electric heater which is connected to an air inlet and a hot air outlet; and a bag which is filled out under a blow pressure given by feeding a hot air from the hot air supplier to discharge the hot air through the surface of the bag and which has flexibility and air-permeability with a resistance of 1.75 to 3.75 $mmH_2O$ to air flow of 0.7 to 1 $m^3/min$.

2. A bed clothes drying device according to claim 1 wherein a peripheral part of the bag is formed with an air-impermeable material or is covered with an air-impermeable sheet.

3. A bed clothes drying device according to claim 1 wherein the upper and lower sheets of the bag have different permeability.

4. A bed clothes drying device according to claim 1 wherein the air-permeability at a specific part of the bag is higher than the other part.

5. A bed clothes drying device according to claim 1 wherein both sheets of the bag are connected with detouchable joint elements.

6. A bed clothes drying device according to claim 1 wherein a plurality of openings are formed on the bag and non-connected joint opening is closed with a plug.

* * * * *

UNITED STATES PATENT AND TRADEMARK OFFICE

CERTIFICATE OF CORRECTION

PATENT NO. : 4,151,658

DATED : May 1, 1979

INVENTOR(S) : SHIGETOSHI HIBINO ET AL

It is certified that error appears in the above-identified patent and that said Letters Patent are hereby corrected as shown below:

Please correct the Priority data to read as follows:

[30] --Dec. 13, 1976 Japan ... 51-166840 [U] and
Feb. 23, 1977 Japan ... 52-20877 [U]-- rather than

[30] "Dec. 13, 1976 Japan ... 51-166840 [U] and
Feb. 23, 1977 Japan ... 52-22087 [U]" as it now appears

Signed and Sealed this

*Sixteenth* Day of *October 1979*

[SEAL]

*Attest:*

RUTH C. MASON
*Attesting Officer*

LUTRELLE F. PARKER
*Acting Commissioner of Patents and Trademarks*